United States Patent [19]
Radisson

[11] Patent Number: 5,326,862
[45] Date of Patent: Jul. 5, 1994

[54] PROCESS FOR THE PREPARATION OF SULPHINYLPRISTINAMYCIN IIB

[75] Inventor: Xavier Radisson, Lyons, France

[73] Assignee: Rhone-Poulenc Rorer S.A., France

[21] Appl. No.: 961,926

[22] PCT Filed: Jul. 15, 1991

[86] PCT No.: PCT/FR91/00580
§ 371 Date: Jan. 14, 1993
§ 102(e) Date: Jan. 14, 1993

[87] PCT Pub. No.: WO92/01693
PCT Pub. Date: Feb. 6, 1992

[30] Foreign Application Priority Data

Jul. 16, 1990 [FR] France .............................. 90 09034

[51] Int. Cl.$^5$ ............................................ C07D 498/16
[52] U.S. Cl. ...................................... 540/456; 540/455
[58] Field of Search ............................... 540/445, 456

[56] References Cited

FOREIGN PATENT DOCUMENTS 2206577 1/1989 United Kingdom ................ 540/456

OTHER PUBLICATIONS

March "Advanced Organic Chemistry" 3rd Ed. (1985) (Wiley) pp. 1089–1090.
Noller "Chemistry of Organic Compounds" 2nd Ed. (1957) (Saunders) pp. 278–279.
European Search Report.

*Primary Examiner*—Robert T. Bond
*Attorney, Agent, or Firm*—Morgan & Finnegan

[57] ABSTRACT

Preparation of (dialkylamino-2 alkyl) sulphinyl-26 pristinamycin II$_B$ by oxidation of (dialkylamino-2 alkyl)-thitinamycin II$_B$, by hydrogen peroxide in the presence of sodium tungstate, in alcoholic medium.

3 Claims, No Drawings

PROCESS FOR THE PREPARATION OF SULPHINYLPRISTINAMYCIN IIB

FIELD OF THE INVENTION

The (2-dialkylaminoalkyl)-26-sulphinylpristinamycin $II_B$ of general formula:

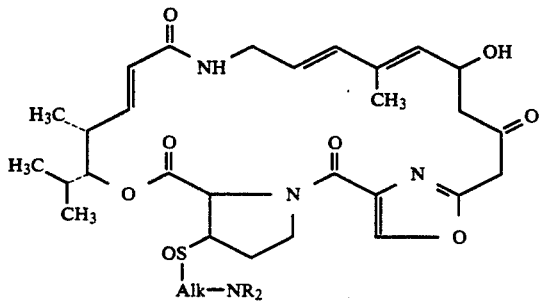

in which Alk represents a straight-chain or branched alkylene radical and R represents straight-chain or branched alkyl radicals, these radicals containing 1 to 10 carbon atoms, are products known for their antibacterial activity and their synergistic action on the antibacterial activity of pristinamycin $I_A$ or alternatively as synthetic intermediates for preparing the corresponding sulphones, as has been described in European Patent 191,662.

DESCRIPTION OF THE INVENTION

The derivatives of pristinamycin $II_B$ of general formula (I) can be obtained by oxidation of the corresponding sulphide, especially according to the teaching of European Patent 191,662 which describes the oxidation of a sulphide of formula:

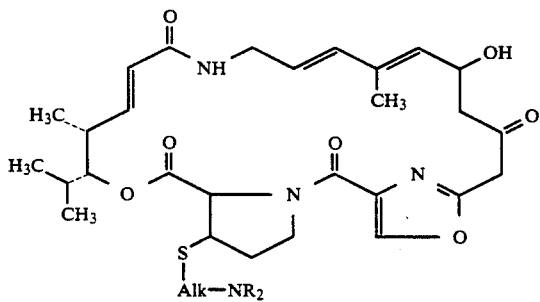

in which Alk and R are as defined above, by an organic or inorganic peracid.

American U.S. Pat. No. 4,775,753 likewise describes the production of (2-dialkylaminoalkyl)-26-sulphinyl-pristinamycin $II_B$ of general formula (I) starting from (2-dialkylaminoalkyl)-26-thiopristinamycin $II_B$ of general formula (II) by oxidation by Oxone.

It has now been found that (2-dialkylaminoalkyl)-26-sulphinylpristinamycin $II_B$ of general formula (I) can be obtained by oxidation of the corresponding sulphide of general formula (II) by hydrogen peroxide, in the presence of sodium tungstate, working in alcoholic medium at a temperature between $-25°$ and $25°$ C.

It is necessary to introduce the oxidizing agent in excess relative to the quantity of product to be oxidized. The hydrogen peroxide employed can be introduced at a rate of 2 to 5 equivalents. Most generally, it is employed at a rate of approximately 2 equivalents per mole of sulphide of pristinamycin $II_B$.

It is understood that the reaction temperature will be fixed as a function of the number of equivalents of oxidizing agent employed. When the reaction is carried out in the presence of 2 equivalents of hydrogen peroxide, the temperature may vary from $-25°$ to $+25°$ C. When the reaction is carried out in the presence of 5 equivalents of oxidizing agent, the reaction is carried out at between $-25°$ and $-10°$ C.

The preferred alcoholic solvent is ethanol, but it is likewise possible to work in methanol or isopropanol.

This process has the advantage of giving access to a product of a higher degree of purity while avoiding purification by chromatography, and thereby allows a very distinct improvement in the yield. Moreover, when the product of formula (I) thus obtained is to be used subsequently for the preparation of (2-dialkylaminoalkyl)-26-sulphonylpristinamycin $II_B$ of general formula:

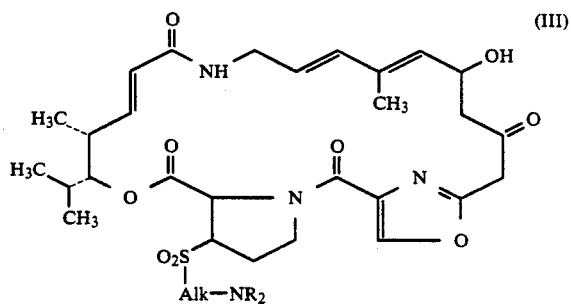

in which Alk and R are as defined above, the derivative of pristinamycin $II_B$ of general formula (I) is of sufficient quality to enable the crude product to be used directly in the subsequent oxidation step, for example according to the process of European Patent Application 252,720, without it being necessary to first carry out chromatography, recrystallization or filtration over silica as was the case for the previously known processes. An improved total yield and likewise a simplification of the implementation of the process result thereby.

EXAMPLES

The following examples, given without implying a limitation, illustrate the present invention.

EXAMPLE 1

2.635 g (4 mM) of (2-diethylaminoethyl)-26-thiopristinamycin $II_B$ isomer A, suspended in 16 cm³ of absolute ethanol, are placed in an ice bath. A solution of 13.2 mg (0.04 mM; 1 mol %) of sodium tungstate dihydrate in 0,906 g (8 mM, 2 equivalents) of hydrogen peroxide (30%) is then added in the course of 2 minutes at a temperature of 1° to 2° C. The suspension of sulphide becomes clear. Stirring is continued for 1 hour and 5 minutes in total.

5 cm³ of water are added to the reaction mixture at 0° C. After stirring for 5 minutes, the solution is extracted with 40 cm³ of methylene chloride. The organic phase is washed 4 tithes with 5 cm³ of water and dried over sodium sulphate. After concentration to dryness, 2.585 g of a pale cream solid are obtained, corresponding to (2-diethylaminoethyl)-26-sulphinylpristinamycin $II_B$ and containing 4% of $A_1$ isomer and 90.3% of $A_2$ isomer (true yield of sulphoxide: 90.3%).

EXAMPLE 2

1.98 g (3 mM [sic]) of (2-diethylaminoethyl)-26-thiopristinamycin $II_B$ isomer A suspended in 12 cm³ of ethanol is cooled to $-20°$ C. and a solution of 9.9 mg (0.03 mM [sic], 1 mol %) of sodium tungstate dihydrate in 1.7 g (15 mM [sic], 5 eq.) of 30% hydrogen peroxide is added thereto in the course of 3 minutes, with stirring.

The temperature of the reaction mixture is kept between $-15°$ and $-20°$ C. while stirring for 1 hour 30 minutes and 3 cm³ of water are added while allowing the temperature to rise to $-10°$ C. 25 cm³ of dichloromethane are added, the organic phase is decanted at 0° C., washed with 5 times 5 cm³ of water, dried over sodium sulphate and concentrated to dryness under reduced pressure to yield the expected (2-diethylaminoethyl)-26-sulphinylpristinamycin $II_B$, mixture of $A_1$ and $A_2$ isomers ($A_1$ 4%; $A_2$ 96%) with a yield of 88%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for the preparation of (2-dialkylaminoalkyl)-26-sulphinylpristinamycin $II_B$ of formula:

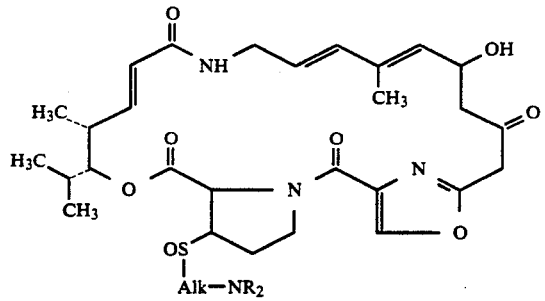

in which Alk represents a straight-chain or branched alkylene radical and R represents straight-chain or branched alkyl radicals, these radicals containing 1 to 10 carbon atoms, comprising oxidation of the corresponding (2-dialkylaminoalkyl)-26-thiopristinamycin $II_B$, of formula:

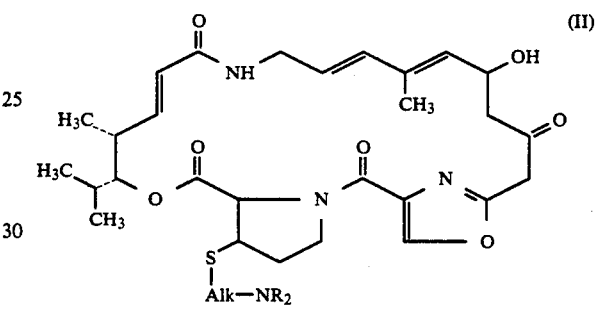

(II)

in which Alk and R are as defined above, by hydrogen peroxide in the presence of sodium tungstate, in alcoholic medium.

2. Process according to claim 1, wherein the reaction is carried out at a temperature between $-25°$ and $+25°$ C. in the presence of equivalents of hydrogen peroxide.

3. Process according to claim 1, wherein the reaction is carried out at a temperature between $-25°$ and $-10°$ C. in the presence of equivalents of hydrogen peroxide.

* * * * *